United States Patent [19]

Ajioka et al.

[11] Patent Number: 5,780,704

[45] Date of Patent: Jul. 14, 1998

[54] PROCESS FOR TREATING PLASTIC PRODUCT

[75] Inventors: Masanobu Ajioka, Kanagawa-ken; Katashi Enomoto, Fukuoka-ken; Akihiro Yamaguchi; Kazuhiko Suzuki, both of Kanagawa-ken, all of Japan

[73] Assignee: Mitsui Chemicals, Inc., Tokyo, Japan

[21] Appl. No.: 68,085

[22] Filed: May 28, 1993

[30] Foreign Application Priority Data

Jun. 4, 1992 [JP] Japan ..................... 4-143940

[51] Int. Cl.$^6$ ..................... A62D 3/00
[52] U.S. Cl. ............. 588/218; 588/204; 588/242; 562/593; 204/520
[58] Field of Search ............. 588/204, 218, 588/242; 562/593; 204/182.4, 520

[56] References Cited

U.S. PATENT DOCUMENTS

| | | | |
|---|---|---|---|
| 4,781,809 | 11/1988 | Falcone, Jr. | 204/182.4 |
| 4,885,387 | 12/1989 | Krochta | 562/515 |
| 4,909,916 | 3/1990 | Koberstein et al. | 204/182.4 |
| 5,034,105 | 7/1991 | Berglund et al. | 204/182.4 |
| 5,132,456 | 7/1992 | King et al. | 562/593 |

FOREIGN PATENT DOCUMENTS

| | | |
|---|---|---|
| 266815 | 5/1988 | European Pat. Off. |
| 2578247 | 9/1986 | France |

*Primary Examiner*—Cecilia J. Tsang
*Assistant Examiner*—C. Delacroix-Muirheid
*Attorney, Agent, or Firm*—Burns, Doane, Swecker & Mathis, L.L.P.

[57] ABSTRACT

A process for decomposing a thermoplastic polymer composition which comprises a polyhydroxycarboxylic acid base polymer as a primary component in an alkaline solution, recovering hydroxycarboxylic acid from the solution by electrodialysis or acid-precipitation and using the recovered hydroxycarboxylic acid for a polymer material, when desired, is provided.

15 Claims, No Drawings

PROCESS FOR TREATING PLASTIC PRODUCT

BACKGROUND OF THE INVENTION AND RELATED ART

1. Field of the Invention

The present invention relates to a process for treating degradable polymer compositions and, more particularly, relates to a process for decomposing thermoplastic polymer compositions primarily comprising a hydroxycarboxylic acid polymer and recovering the hydroxycarboxylic acid and for optionally using recovered hydroxycarboxylic acid for a raw material of a polymer.

2. Related Art of the Invention

Polyethylene, polypropylene, polyethylene terephthalate, polyvinyl chloride, paper, aluminum or composite materials of these resins have been conventionally used for packaging materials. However these packaging materials prepared from these polymers have a very slow rate of degradation and thus remain semipermanently when discarded as refuse and buried under the ground. Disposal of these materials in the ocean causes aesthetic damage of a view or destruction of the living environment of marine organisms.

On the other hand, polyhydroxy carboxylic acid or copolymers of hydroxycarboxylic acids (which will hereinafter be referred to simply as a hydroxycarboxylic acid base polymer) have been developed as thermoplastic polymers having biodegradability. These polymers can be completely biodegraded within a few months to an year in an animal body. When the polymers are placed in soil or sea water, they start to decompose within a few weeks in a moist environment and disappear within several years. Further, final degradation products of these polymers are lactic acid, carbon dioxide and water which are nontoxic to the human body.

Polymers of lactic acid are usually prepared from a cyclic dimer of lactic acid which is called lactide, and U.S. Pat. Nos. 1,995,970, 2,362,511, and 2,683,136 have disclosed a polymerization process of lactide. U.S. Pat. No. 3,636,956 and 3,797,499 have disclosed a process from copolymerizing lactic acid and glycolic acid. In the copolymerization of lactic acid and other hydroxy carboxylic acid copolymer, lactide and a cyclic ester intermediate, for example glycolide, i.e., a dimer of glycolic acid, are mixed and ring-opening polymerization is carried out.

Wastes of the above degradable polymer, however, must be generally transported to a remote landfill area in order to bury these wastes under the ground. It also requires a considerable long time to degrade these wastes in a buried state. Problems on shortage of the landfill area cannot be solved with ease. Even in the case of treating these wastes by incineration, transfer of these materials to an incineration facility is needed, and a specially designed incinerator must be installed in the neighborhood of waste-generating places. When these wastes are contaminated with hazardous materials such as putrefied organic materials or pathogenic microorganisms, special counter measures for protecting from bad smell or infection are required for the transfer of these wastes to a disposal facility.

Particularly when the wastes are contaminated with pathogenic microorganisms, common landfill disposal leads to danger of spreading infectious diseases and incineration becomes a requisite treatment. Incineration, however, cannot recover monomers which constitutes wasted polymer and is unfavorable in economy.

SUMMARY OF THE INVENTION

One object of the invention is to provide a process for decomposing a thermoplastic polymer composition primarily comprising a polyhydroxycarboxylic acid base polymer, a polylactic acid base polymer in particular, safely in simple equipment to obtain a solution, recovering hydroxycarboxylic acid from the solution, and optionally reusing said hydroxycarboxylic acid for a raw material of the polymer.

As a result of an intensive investigation on a treating process of a polymer primarily comprising a hydroxycarboxylic acid base polymer, the present inventors have found that the hydroxycarboxylic acid base polymer is decomposed with ease to the monomer unit in an alkaline solution of pH 10 or more, that the polymer can be decomposed while maintaining the configuration as intact when the hydroxycarboxylic acid has an asymmetric carbon, that the hydroxy carboxylic acid can be recovered from the solution, and that the recovered hydroxycarboxylic acid can be optionally reused for a raw material of the polymer. Thus the invention has been completed.

The invention can provide an effective and industrially useful process for treating and decomposing a hydroxycarboxylic acid base thermoplastic polymer composition in an alkaline solution, recovering hydroxycarboxylic acid from the solution and reusing, when desired, the recovered acid for a raw material of the polymer. When the hydroxycarboxylic acid in the polymer has an asymmetric carbon, the hydroxycarboxylic acid can be recovered while maintaining the configuration as intact. Consequently, the proportion of an optically active unit in the polymer can be controlled with ease even though the recovered acid is reused for a raw material of the polymer.

DETAILED DESCRIPTION OF PREFERRED EMBODIMENTS

The present invention is a process for decomposing a thermoplastic polymer composition primarily comprising a homopolymer or copolymer of hydroxycarboxylic acid to the monomer unit in an alkaline solution of pH 10 or more. When the hydroxycarboxylic acid in the polymer has an asymmetric carbons the polymer is decomposed in the step while maintaining the configuration as intact. Hydroxycarboxylic acid is recovered from the solution and reused, when desired, for a raw material of the polymer.

The invention uses a hydroxycarboxylic acid polymer as a primary component. Hydroxycarboxylic acids which can be used include, for example, lactic acid, glycolic acid, 3-hydroxybutyric acid, 4-hydroxybutyric acid, 4-hydroxyvaleric acid, 5-hydroxyvaleric acid and 6-hydroxycaproic acid.

The hydroxycarboxylic acid polymer can be obtained by (1) a direct dehydrating polycondensation process of hydroxycarboxylic acid, (2) a ring-opening polymerization process of a cyclic dimer such as lactide, the cyclic dimer of lactic acid, or glycolide (GLD), the cyclic dimer of glycolic acid, (3) a ring-opening polymerization process of ε-caprolactone (CL), the cyclic ester of 6-hydroxycaproic acid, or (4) a ring-opening polymerization process of a mixture of these raw materials. When these cyclic compounds are used as raw materials, recovered hydroxycarboxylic acids must be converted again to cyclic compounds.

No particular limitation is imposed upon the average molecular weight of the hydroxycarboxylic acid polymer. Polymers having an average molecular weight of 10,000~1,000,000 are generally used for applications which require strength. When the molecular weight is less than 10,000, the strength of films or molded articles becomes too low. On the other hand, a molecular weight of more than 1,000,000 leads to high melt viscosity and poor processability.

A thermoplastic polymer composition is usually prepared by mixing a hydroxycarboxylic acid base polymer with a known thermoplastic polymer or plasticizer and various modifiers. The proportion of the hydroxycarboxylic acid base polymer in the thermoplastic polymer composition depends upon the desired degradability and is preferably 50% or more.

The alkaline solution used for decomposition of the thermoplastic polymer composition in the invention can be prepared by adding an inorganic base to an aqueous solvent. The inorganic bases which can be used include, for example, aqueous ammonia, hydroxide, oxide and carbonate of alkali metals such as sodium and potassium and hydroxide and oxide of alkaline earth metals such as calcium, magnesium and barium. These inorganic bases can be used in the form of an aqueous solution or suspension. Sodium hydroxide or potassium hydroxide is usually preferred in view of economy and hydroxycarboxylic acid recovery.

The alkaline solution used in the invention has a pH 10 or more. In the case of pH 9 or less, it takes a very long time to completely hydrolyze the polymer to the monomer. Such conditions are not suitable for practical use.

No particular limitation is placed on the concentration of the alkaline solution. Higher concentration are preferred because of a quick decomposition rate. A concentration are of 1% or more is generally used. The alkaline solution can be repeatedly used for decomposition treatment of the polymer. When the alkaline component in the solution is consumed for the treatment, the alkaline component must be added to maintain alkalinity of the solution at pH 10 or more. Higher treatment temperature results in a quicker decomposition rate of the polymer. Decomposition is usually carried out at temperature of 40° C. or more, although no particular restriction is imposed upon the temperature. The alkaline solution of the invention can contain organic solvents such as alcohol.

Hydroxycarboxylic acid in the solution obtained above by alkaline treatment of the hydroxycarboxylic acid base polymer maintains its configuration in the polymer even though an asymmetric carbon is present.

Medical devices or other articles which are made of the thermoplastic polymer composition of the invention and used in hospitals or applied to uses which bring these articles into contact with excretions of human and animals, are liable to be contaminated with pathogenic microorganisms and must be treated under special caution when abandoned. The treatment process of the invention can make the pathogenic microorganisms extinct in the course of polymer decomposition even though contaminated with these organisms and can prevent spreading of contamination with these hazardous materials. Thus, the process can be used as a suitable treatment.

The treatment of the invention can be carried out by charging the alkaline solution to a conventional tank or vessel equipped with a stirrer, successively adding molded articles of the polymer with warming or at room temperature and maintaining the mixture for a prescribed time. The molded articles of the polymer can be added as intact or after crushing into coarse or fine particles.

In the process of the invention, hydroxycarboxylic acid is recovered from the solution after decomposition by the following processes.

(1) Sodium hydroxide decomposition-electrodialysis process

When an aqueous sodium hydroxide solution is used as the alkaline solution, an aqueous hydroxycarboxylic acid solution can be efficiently obtained by electrodialysis. Electrodialysis is carried out with equipment having an ion exchange membrane and electrodes. Exemplary equipment includes Aquatech (trade mark of Allied Chem. Co.) and exemplary ion exchange films include Nafion film (trade mark of Du pont Chem. Co.) or Selemion film (trade mark of Asahi Glass Chem. Co.). Higher concentration of a hydroxycarboxylate solution leads to higher efficiency of the electrodialyser. Thus, the solution obtained by the decomposition is preferably concentrated before dialysis when the solution has a low concentration. Treatment with the alkaline solution is preferably carried out so as to obtain a higher concentration of hydroxycarboxylate.

(2) Calcium hydroxide decomposition-crystallization process

When the hydroxycarboxylic acid of the invention is lactic acid, an aqueous solution or suspension of calcium hydroxide is used as an alkaline solution. Isolation of calcium lactate from the aqueous solution obtained by decomposition can be efficiently carried out by using calcium hydroxide. For example, a polymer is added to an aqueous suspension of calcium hydroxide and completely decomposed with stirring at 50~100° C. Unreacted calcium hydroxide is removed from the reaction mixture by such means as filtration. The filtrate is cooled and precipitated calcium lactate is filtered. Calcium lactate thus obtained is dissolved again in water and an equivalent amount of sulfuric acid to calcium is added to the aqueous solution. Precipitated calcium sulfate is filtered off and an aqueous lactic acid solution almost free from calcium can be thus obtained.

The aqueous hydroxycarboxylic acid or lactic acid solution obtained contains traces of cations such as sodium and calcium and anions such as sulfate ion. The solution can be further purified with an ion exchange resin when high purity products are required.

The process of the invention, however, is usually carried out at relatively low temperatures and hence by-products are formed in a small amount in the decomposition and recovery steps. As a result, hydroxycarboxylic acid can be recovered in high purity. Recovered hydroxycarboxylic acid can be used again as a raw material of polymer without purification in particular. When hydroxycarboxylic acid has an asymmetric carbon, the hydroxycarboxylic acid can be recovered as a monomer while maintaining the configuration in the polymer as intact. Consequently, the proportion of optically active component in the polymer prepared from the recovered hydroxycarboxylic acid can be controlled with ease. For example, almost pure L-lactic acid can be recovered from a L-lactic acid polymer and polylactic acid prepared from the recovered L-lactic acid contains almost no D-lactic acid.

EXAMPLES

The present invention will hereinafter be illustrated in detail by way of examples and comparative examples.

In the examples and comparative examples, molecular weight and composition of D- and L-lactic acid were analyzed by the following methods.

(1) Molecular weight

An weight average molecular weight of the polymer was measured by gel permeation chromatography under the following conditions using polystyrene as a reference.

Equipment: Shimadzu LC-10 AD
Detector: Shimadzu RID-6A
Column: Hitachi Kasei GL-S350DT-5, GL-S370DT-5
Solvent: Chloroform
Concentration: 1%
Amount of sample: 20 μl
Flow rate: 1.0 ml/min (2) Composition of D- and L-lactic acid Polymer was hydrolyzed by maintaining in a 5N aqueous sodium hydroxide solution at 60° C. for 10 hours. L-lactic acid in the solution thus obtained was oxidized to pyruvic acid by the action of L-lactic acid dehydrogenase and nicotinamide adenine dinucleotide (hereinafter referred to as NAD). L-lactic acid was determined by measuring through absorptiometry the amount of NADH which was formed by reduction of NAD in the reaction. On the other hand, D-lactic acid was also determined by a similar action of D-lactic acid dehydrogenase and NAD. The composition was obtained by calculating the ratio of L-lactic acid to D-lactic acid. Separately, L-lactic acid was confirmed to cause no racemization under the hydrolysis conditions by maintaining L-lactic acid in a 5N aqueous sodium hydroxide solution for 10 hours.

Next, preparation processes of the polymer and its film used in the examples will be illustrated by preparation examples.

Preparation Example 1

To a thick-walled cylindrical stainless steel polymerizer equipped with a stirrer, 216g (1.5 mol) of L-lactide, 0.01% by weight of stannous octoate and 0.03% by weight of dodecyl alcohol were charged. The mixture was deaerated for 2 hours under vacuum and heated in a nitrogen atmosphere with stirring at 200° C. for 3 hours. Then the polymerizer was gradually deaerated for 2 hours under vacuum and heated receiver with a vacuum pump to a reduced pressure of 3 mm Hg while maintaining the same temperature. After reacting for an hour from the start of deaeration, distillation of monomer and low molecular weight volatiles were ceased. The interior of the polymerizer was replaced with nitrogen. Poly-L-lactic acid obtained was discharged from the bottom of the polymerizer in the form of a strand and cut into pellets. The pelletized polymer had an average molecular weight of 100,000 and a L-lactic acid/D-lactic acid ratio of 99.5 : 0.5.

Preparation Example 2

Polylactic acid pellets were prepared by carrying out the same procedures as described in Preparation Example 1 except that 216 g of L-lactide was replaced by 172 g of L-lactide and 44 g of DL-lactide. The polymer obtained had an average molecular weight of 100,000.

Preparation Example 3

L-Lactide-glycolide copolymer pellets were prepared by carrying out the same procedures as described in Preparation Example 1 except that 216 g of L-lactide was replaced by 108 g of L-lactide and 108 g of glycolide. The copolymer obtained had an average molecular weight of 100,000.

Preparation Example 4

L-lactide-ε-caprolactone copolymer pellets were prepared by carrying out the same procedures as described in Preparation Example 1 except that 216 g of L-lactide was replaced by 108 g of L-lactide and 108 g of ε-caprolactone. The copolymer obtained had an average molecular weight of 70,000.

Preparation Example 5

In a reaction vessel, 10.0 kg of 90% L-lactic acid was heated with stirring at 150° C. for 3 hours under reduced pressure of 50 mm Hg while distilling out water. Thereafter 6.2 g of tin powder was added and further reacted with stirring at 150° C. for 2 hours under reduced pressure of 30 mm Hg to obtain an oligomer. To the oligomer, 28.8 g tin powder and 21.1 kg of diphenyl ether were added, and an azeotropic dehydration reaction was carried out at 150° C. under reduced pressure of 35 mm Hg. Distilled water was separated from the solvent in a water separator and the solvent alone was returned to the reaction vessel. After reacting for 2 hours, the route of the returning solvent was changed to pass through a column packed with 4.6 kg of molecular sieve 3A before returning to the reaction vessel. Successively, the reaction was continued at 150° C. for 40 hours under reduced pressure of 35 mm Hg to obtain a polylactic acid solution having an average molecular weight of 110,000. The solution obtained was mixed with 44 kg of dehydrated diphenyl ether and cooled to 40° C. Precipitated crystals were filtered, washed three times with 10 kg of n-hexane and dried at 60° C. under reduced pressure of 50 mm Hg. The powder thus obtained was mixed with 12 kg of 0.5 N hydrochloric acid and 12.0 kg of ethanol, stirred at 35° C. for an hour, filtered and dried at 60° C. under reduced pressure of 50 mm Hg to obtain 6.1 kg of polylactic acid powder (85% yield). The powder was pelletized with a pelletizer and used for measuring properties. The polymer obtained had an average molecular weight of 110,000 and a L-lactic acid/D-lactic acid ratio of 98.5 : 1.5.

Preparation Example 6

L-Lactic acid-glycolic acid copolymer pellets were prepared by carrying out the same procedures as described in Preparation Example 5 except that 10.0 kg of 90% L-lactic acid was replaced by 9.0 kg of 90% L-lactic acid and 1.3 kg of 70% glycolic acid. The copolymer obtained had an average molecular weight of 100,000.

The polymers obtained in Preparation Examples 1-6 were individually dissolved in chloroform in a concentration of 10-20%, cast respectively on a glass plate and dried at 60° C. under reduced pressure. Films thus prepared had a thickness of 25-30 μm and were used in the following examples.

Example 1

A film which was obtained from the polymer of Preparation Example 1 and had dimensions of 150 mm in length, 150 mm in width and 30 μm in thickness was submerged into 50 ml of a 4% aqueous sodium hydroxide solution and maintained at 60° C. for an hour. The film was completely dissolved. The solution had pH of 12 or more during the treatment. According to an HLC. analysis of the reaction mixture, the amount of lactic acid formed was almost equivalent to the lactic acid units in the polymer.

Example 2

The same procedures as described in Example 1 were carried out except that the polymer of Preparation Example 1 was replaced by the polymer of Preparation Example 2. The film was completely dissolved. The solution had pH 12 or more. According to an HLC. analysis of the reaction mixture, the amount of lactic acid formed was almost equivalent to the lactic acid units in the polymer.

Example 3

The same procedures as described in Example 1 were carried out except that the 4% aqueous sodium hydroxide solution was replaced by a 5% aqueous calcium hydroxide suspension. After finishing the reaction the reaction mixture was filtered with a 10 mesh sieve and film residue was not found. The filtrate had a pH of 12 or more during the treatment. According to an HLC. analysis of the reaction mixture, the amount of the lactic acid formed was almost equivalent to the lactic acid units in the polymer.

Example 4

A film which was obtained from the polymer of Preparation Example 3 and had dimensions of 150 mm×150 mm×25 μm was submerged in 50 ml of a 5% aqueous ammonia solution and maintained at 40° C. for 5 hours. The film was completely dissolved. The solution had a pH of 12 or more during the treatment. According to an HLC. analysis of the reaction mixture, the amount of lactic acid and glycolic acid are individually almost equivalent to the lactic acid units in the polymer.

Example 5

A film which was obtained from the polymer of Preparation Example 4 and had dimensions of 150 mm×150 mm×25 μm was submerged in 50 ml of a 10% aqueous potassium hydroxide solution and maintained at 60° C. for 5 hours. The film was completely dissolved. The solution had a pH of 12 or more during the treatment. According to the HLC. analysis of the reaction mixture, the amounts of lactic acid and ε-caproic acid formed were individually almost equivalent to the lactic acid unit and ε-caproic acid unit in the polymer.

Example 6

*Escherichia coli* was attached on a film which was obtained from the polymer of Preparation Example 1 and had dimensions of 150 mm×150 mm×30 μm was submerged in 50 ml of a 4% aqueous sodium hydroxide solution. After maintaining the mixture at 60° C. for 5 hours, the film was completely dissolved. The solution had a pH of 12 or more during the treatment. According to an HLC. analysis of the reaction mixture, the amounts of lactic acid formed was almost equivalent to the lactic acid unit in the polymer. *Escherichia coli* was not detected in the solution after treatment.

Example 7

In 1 l of a 5 N aqueous sodium hydroxide solution, 200 g of pellets of the polymer prepared in Preparation Example 5 was submerged and maintained at 80° C. for 2 hours. The solution was maintained at a pH of 12 or more during the reaction. The pellets were completely dissolved. According to an HLC. analysis of the resulting solution, the amount of the lactic acid formed was almost equivalent to the lactic acid units in the polymer. The L-lactic acid/D-lactic acid ratio in the resulting solution was 98.5:1.5 and indicated that the configuration of asymmetric carbon in the lactic acid polymer was retained.

Next, the hydrolysis solution thus obtained was concentrated to 600 ml. A electrodialysis equipment comprises a cathode cell and an anode cell, both cells are separated by Selemion type CMR cation exchange membrane of which has an effective area of 9 cm². Electrodialysis was carried out while the concentrated solution was circulated to the anode cell and aqueous sodium hydroxide solution was circulated to the cathode cell. 552 g of 43% L-lactic acid solution was obtained by electrodialysis (95% yield based on the polymer used).

The solution was further concentrated and used as lactic acid for polymerization. Polymerization of the recovered lactic acid monomer was carried out by the same procedures as described in Preparation Example 6 to obtain a polymer having an average molecular weight of 100,000.

Comparative Example 1

An 1 N aqueous sodium hydroxide solution was adjusted to pH 9 by addition of an 1 N aqueous hydrochloric acid solution. Into 100 ml of the solution thus obtained, 20 g of the polymer pellets obtained in Preparation Example 5 was submerged and maintained at 80° C. for 2 hours. The polymer pellets which almost maintained their original shape were 15 g. According to an HLC. analysis, the solution contained 1 g of lactic acid after the treatment. The solution after the treatment had a L-lactic acid/D-lactic acid ratio of 98.6:1.4.

Example 8

Into 1 l of a 5 N aqueous sodium hydroxide solution, 200 g of polymer pellets obtained in Preparation Example 6 were submerged at 80° C. for 2 hours. The pellets were completely dissolved. The resulting solution was concentrated to 600 ml and subjected to electrodialysis with the same equipment as used in Example 7. The solution thus obtained was 540 g and contained 217 g of L-lactic acid and 24 g of glycolic acid.

The solution was further concentrated and subjected to polymerization by the same procedures an described in Example 6. A polymer having an average molecular weight of 90,000 was obtained.

Example 9

Into 1 of a 10% aqueous calcium hydroxide suspension, 100 g of polymer pellets obtained in Preparation Example 1 was submerged and maintained at 80° C. for 2 hours. The solution was kept in at a pH of 12 or more during the treatment. The pellets were completely dissolved. Undissolved calcium hydroxide was filtered off. The filtrate contained almost equivalent of lactic acid to the lactic acid unit in the polymer according to an HLC. analysis. The filtrate had a L-lactic acid/D-lactic acid ratio of 99.5:0.5 and thus the configuration of lactic acid in the polymer was maintained. The solution was concentrated and allowed to stand overnight at 10° C. Precipitated calcium lactate crystals were isolated by filtration and dissolved in the same amount of water at 65° C. An equivalent amount of 98% sulfuric acid was added to the aqueous solution and precipitated calcium sulfate was filtered off. The filtrate was concentrated under reduced pressure to obtain an 88% aqueous L-lactic acid solution. The yield was 84%.

The solution was further concentrated was subjected to polymerization by the same procedures as described in Preparation Example 6. A polymer having an average molecular weight of 100,000 was obtained.

The present invention may be practiced or embodied in still other ways without departing from the spirit or essential character thereof. However, these examples are not intended to limit the scope of the present invention.

We claim:

1. A process for decomposing a thermoplastic polymer composition consisting essentially of a homopolymer or copolymer of hydroxycarboxylic acid selected from the group consisting of lactic acid, glycolic acid and 6-hydroxycaproic acid and having a weight average molecular weight of 10,000 to 1,000,000 comprising contacting the polymer composition with an alkaline solution of pH 10 or more whereby the homopolymer or copolymer is decomposed to produce hydroxycarboxylic acid and recovering the hydroxycarboxylic acid from the solution.

2. The process of claim 1 wherein the thermoplastic polymer composition has an asymmetric carbon configuration and the hydroxycarboxylic acid is recovered while maintaining the asymmetric carbon configuration.

3. The process of claim 1 wherein the hydroxycarboxylic acid is lactic acid.

4. The process of claim 1 wherein the thermoplastic polymer composition consists essentially of a copolymer of hydroxycarboxylic acid which comprises two or more monomers selected from lactic acid, glycolic acid and 6-hydroxycaproic acid.

5. The process of claim 1 wherein the thermoplastic polymer composition is contaminated with hazardous materials.

6. The process of claim 5 wherein the hazardous materials are pathogenic microorganisms.

7. The process of claim 1 wherein the hydroxycarboxylic acid is recovered from the solution by electrodialysis.

8. The process in claim 7 wherein the hydroxycarboxylic acid is lactic acid.

9. The process of claim 7 wherein the thermoplastic polymer composition consists essentially of a copolymer of hydroxycarboxylic acid which comprises two or more monomers selected from lactic acid, glycolic acid and 6-hydroxycaproic acid.

10. The process of claim 7 wherein the thermoplastic polymer composition is contaminated with hazardous materials.

11. The process of claim 10 wherein the hazardous materials are pathogenic microorganisms.

12. A process for decomposing a thermoplastic polymer composition consisting essentially of lactic acid polymer having a weight average molecular weight of 10,000 to 1,000,000 comprising contacting the polymer with a calcium hydroxide solution having a pH of 10 or more, separating calcium lactate from the solution and converting calcium lactate to lactic acid by addition of sulfuric acid, and recovering lactic acid.

13. The process of claim 12 wherein the thermoplastic polymer composition is contaminated with hazardous materials.

14. The process of claim 13 wherein the hazardous materials are pathogenic microorganisms.

15. A process for decomposing a thermoplastic polymer composition consisting essentially of a homopolymer or copolymer of hydroxycarboxylic acid selected from the group consisting of lactic acid, glycolic acid and 6-hydroxycaproic acid and having a weight average molecular weight of 10,000 to 1,000,000 comprising contacting the polymer composition with an alkaline solution of pH 10 or more whereby the homopolymer or copolymer is decomposed to produce hydroxycarboxylic acid, recovering the hydroxycarboxylic acid from the solution and using the recovered hydroxycarboxylic acid to prepare a polymer material.

* * * * *